(12) United States Patent
Fox

(10) Patent No.: US 10,092,718 B2
(45) Date of Patent: Oct. 9, 2018

(54) METHODS AND APPARATUS FOR HIGH FREQUENCY PULMONARY VENTILATION

(71) Applicant: Donald Fox, Phoenix, AZ (US)

(72) Inventor: Donald Fox, Phoenix, AZ (US)

(73) Assignee: Donald Fox, Phoenix, AZ (US)

( * ) Notice: Subject to any disclaimer, the term of this patent is extended or adjusted under 35 U.S.C. 154(b) by 552 days.

(21) Appl. No.: 14/074,635

(22) Filed: Nov. 7, 2013

(65) Prior Publication Data

US 2015/0122259 A1 May 7, 2015

(51) Int. Cl.
*A61M 16/00* (2006.01)
*A61M 16/20* (2006.01)

(52) U.S. Cl.
CPC .... *A61M 16/0075* (2013.01); *A61M 16/0096* (2013.01); *A61M 16/20* (2013.01); *A61M 2016/0027* (2013.01); *A61M 2205/0272* (2013.01); *A61M 2205/106* (2013.01); *A61M 2205/502* (2013.01)

(58) Field of Classification Search
CPC .. A61M 16/00–16/0096; A61M 16/08; A61M 2016/0015–2016/0042; F04B 43/00–43/046; F04B 45/00–45/027; F04B 45/04–45/067; F04B 45/10
See application file for complete search history.

(56) References Cited

U.S. PATENT DOCUMENTS

| | | | |
|---|---|---|---|
| 3,333,603 A * | 8/1967 | Wentworth | A61M 16/00 128/205.16 |
| 4,157,092 A * | 6/1979 | Fare | A61M 16/00 128/202.27 |
| 4,719,910 A | 1/1988 | Jensen | |
| 5,007,420 A * | 4/1991 | Bird | A61M 16/00 128/200.14 |
| 5,542,416 A * | 8/1996 | Chalvignac | A61M 16/00 128/204.23 |
| 6,085,746 A | 7/2000 | Fox | |
| 6,279,574 B1 * | 8/2001 | Richardson | A61M 16/0096 128/204.17 |
| 2007/0113843 A1 * | 5/2007 | Hughes | A61M 16/0057 128/200.24 |
| 2010/0180899 A1 * | 7/2010 | Capezzuto | A61M 16/20 128/205.24 |

OTHER PUBLICATIONS http://www.doorking.com/access-controls/magnetic-door-locks.php.

* cited by examiner

*Primary Examiner* — Gregory Anderson
*Assistant Examiner* — Ned T Heffner
(74) *Attorney, Agent, or Firm* — Jennings, Strouss & Salmon PLC; Michael K. Kelly; Daniel R. Pote

(57) ABSTRACT

Pulmonary ventilator methods and systems are provided winch include a housing having a user interface control panel; a pneumatic circuit for delivering a high frequency pressure wave from the housing to a patient lung; a variable volume disposed within the housing including a stationary plate secured to the housing and a reciprocating plate pivotably mounted with respect to the stationary plate; and a magnet assembly disposed within the housing and configured to pivot the reciprocating plate. The variable volume may also include a resiliently contractible section extending between and joining a portion of the stationary plate and a portion of the reciprocating plate, wherein the resiliently contractible section may be in the form of a bellows and/or a pleated material.

14 Claims, 5 Drawing Sheets

METHODS AND APPARATUS FOR HIGH FREQUENCY PULMONARY VENTILATION

TECHNICAL FIELD

The present invention generally relates to pulmonary ventilation, and more particularly to a wedge shaped oscillating volume adapted to communicate a high frequency pressure wave to the patient airway.

BACKGROUND

Presently known oscillating ventilator systems are described in Jenson U.S. Pat. No. 4,719,910 and Fox U.S. Pat. No. 6,085,746. Presently known ventilators used in the ventilation of mammals, particularly humans, supply an air or air/oxygen mixture through a tube to the patient's lungs. A variable air volume is manipulated, for example, using magnets, to create an alternating inspiratory and expiratory pressure wave to the lungs. As a result of the high oscillation frequency necessary for effective ventilation, the air becomes heated, making it difficult to maintain proper temperature and humidity levels in the entrained air.

Moreover, presently known ventilators are limited in their ability to consistently deliver a high frequency pressure wave at high air volumes needed for larger adults, as well as the low air volumes needed for smaller body weight and neo-natal patients.

Accordingly, systems and methods are needed which address these limitations.

SUMMARY OP THE INVENTION

In accordance with various embodiments of the present invention, methods and apparatus are provided for high frequency pulmonary ventilation employing a wedge shaped variable volume. The wedge shaped volume includes a fixed plate and a pivoting plate joined on the side edges by pleated retractable bellows, and joined at the top by a semi-cylindrical adapter which communicates pneumatically with patient air supply circuit. A first electromotive sub-system analogous to an electromagnetic door lock is used for the primary movement of the pivoting plate of the wedge shaped variable volume. If necessary, a second electromotive sub-system including at least one rare earth magnet and a corresponding coil is used to nudge the pivoting plate into magnetic engagement with the first electromotive sub-system.

BRIEF DESCRIPTION OF THE DRAWING FIGURES

A more complete understanding of the subject matter may be derived by referring to the detailed description and claims when considered in conjunction with the following figures, wherein like reference numbers refer to similar elements throughout the figures, and:

DETAILED DESCRIPTION OF PREFERRED EXEMPLARY EMBODIMENTS

Embodiments of the subject matter described herein generally relate to systems and methods for the ventilation of mammals, and particularly the full human size range from infant to large adults. The methods and devices described herein are useful for ventilation when the pulmonary system is in distress and unable to function adequately without assistance and particularly in the presence of traumatic chest wound or wounds where the airways of the lung or lungs are connected to the thoracic pleural cavity, as well as for pneumothoracies due to various causes including conventional ventilator induced barotraumas.

The present invention involves high frequency ventilation where the rate exceeds the normal breathing rate of the subject being treated. The high frequency pressure wave includes both positive (inspiratory) and negative (expiratory) amplitude where the positive portion of the wave is adjustable from approximately three tenths (30%) to approximately seven tenths (70%) of the period (duty cycle) of the wave.

An embodiment employs a contained volume of air in the form of a triangular or trapezoidal prism where one or both of the rectangular sides of the prism can be cycled toward and away from its centerline. This displacement alternately increases and decreases the pressure within the volume, which communicates with the patient's lung to deliver a pressure wave of desired amplitude, frequency, and duty cycle. Various electromechanical and magnetic mechanisms are used to provide the impetus for the movement of the contained variable air volume, as described in more detail below.

Figure 1:
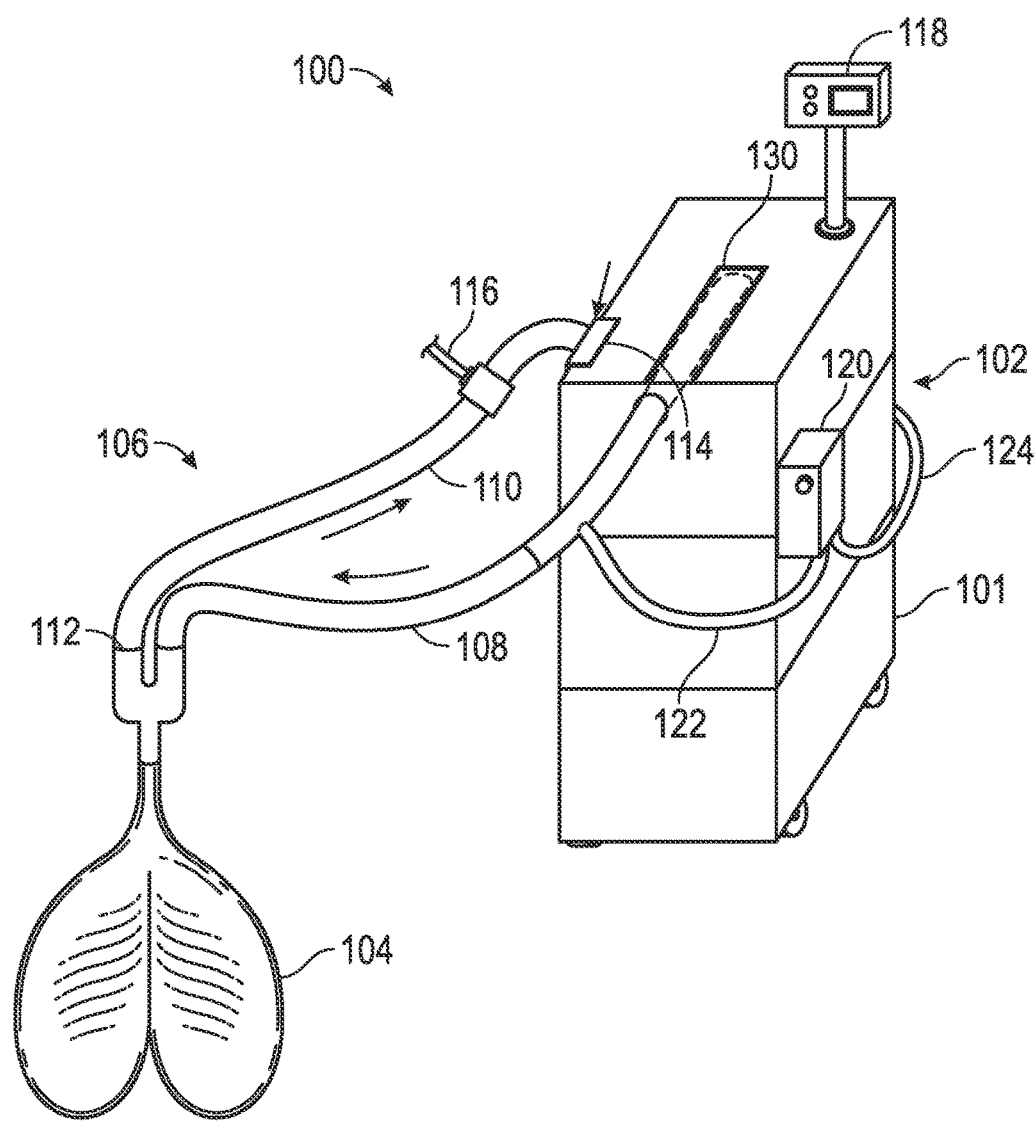
FIG. 1 is a schematic layout view of a pulmonary ventilator system in accordance with an embodiment.

FIG. 1 is a schematic layout view of a pulmonary ventilator system 100 in accordance with an embodiment. More particularly, pulmonary ventilator system 100 includes a ventilator 102 for supplying a high frequency pressure wave to a patient's lungs 104 through a pneumatic circuit 106. Pneumatic circuit 106 includes an inspiratory tube 108, an expiratory tube 110, a proximal pressure sensor 112 disposed near the patient's lungs 104, a positive end expirator pressure (PEEP) valve 114 for regulating and providing a low pass frequency control for the mean the pressure within the pneumatic circuit 106, and a safety valve 116. All or a portion of the pneumatic circuit may be disposable and made from a medical grade plastic or rubber material.

Ventilator 102 includes a housing 101 within which the oscillating volume is contained, a control panel 118 for facilitating user input and for displaying various control and operating parameters, and a humidifier for supplying water from a water source 120, and a delivery conduit 122 for introducing humidified gas (e.g., air/oxygen mixture) into the inspiratory tube 108. Ventilator 102 further includes an adapter 130 configured to connect the inspiratory tube 108 to the internal oscillating air volume, as described in greater detail below in conjunction with FIG. 2.

Figure 2:
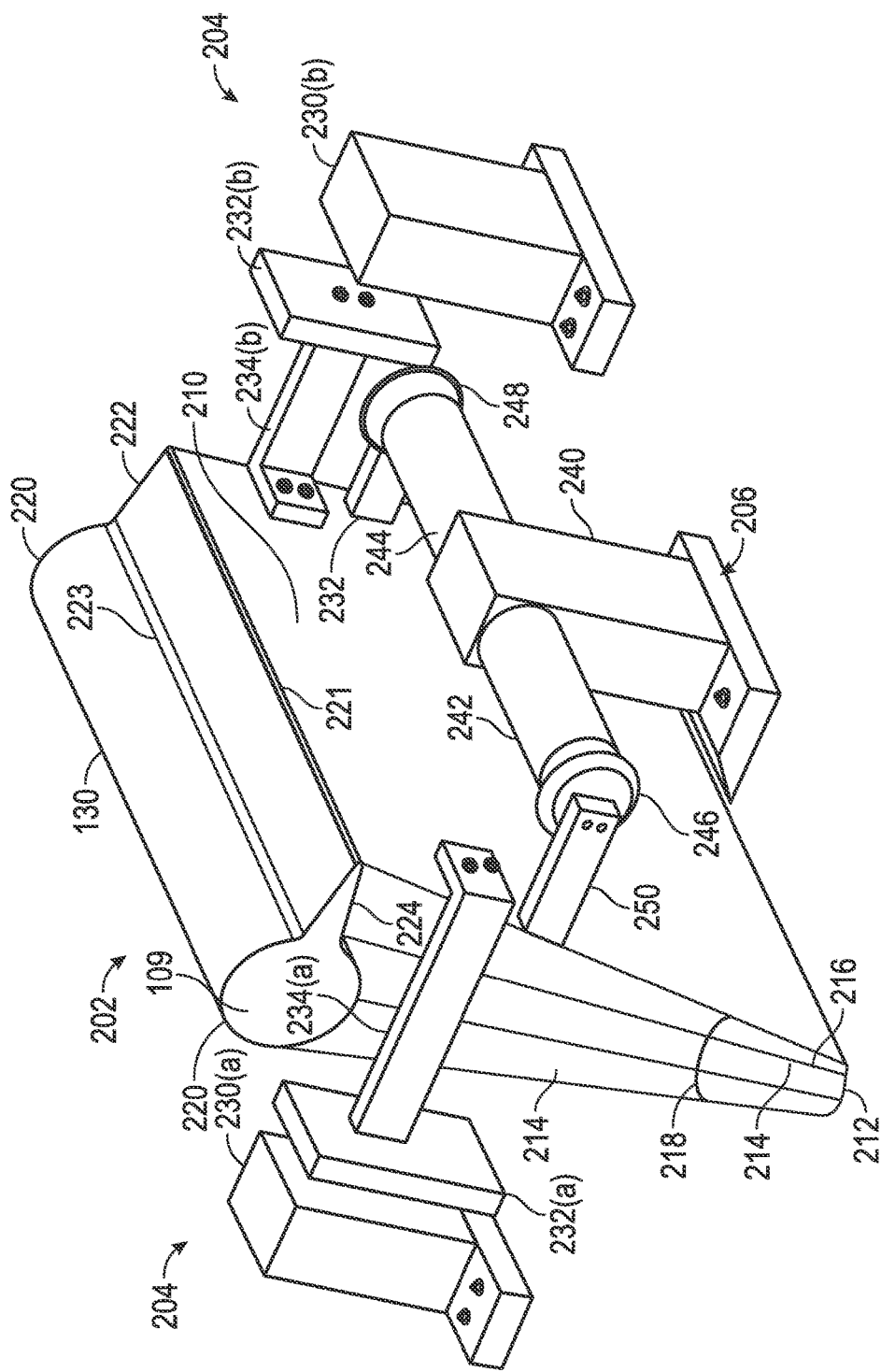
FIG. 2 is a perspective view of a wedge shaped oscillating volume including primary and supplemental motive sub-systems in accordance with a preferred embodiment.

FIG. 2 is a perspective view of a wedge shaped oscillating volume 202 including a primary motive sub-system 204 and a supplemental motive sub-system 206 in accordance with a preferred embodiment. More particularly, wedge shaped oscillating volume 202 includes a pair of rectangular, trapezoidal, or other suitably configured plates 210 joined together by pleated bellows (or other low inch on seam) 214 having one or more pleats 216 or other suitable material which permits the wedge volume to expand and contract. Only the front plate 210 is visible in FIG. 2; the rear plate is obscured from view. The rear plate is secured to and stationary within the ventilator housing 101. The front plate 210 is configured to oscillate back and forth about a variable angle 218, alternately expanding and contracting the suitably triangular or trapezoidal carbon fiber bellows 214, as described in greater detail below. If desired, a disposable or reusable liner may be inserted into the volume 202 to avoid patient to patient contamination.

The wedge shaped oscillating volume 202 further includes the semi-cylindrical adapter 130 which connects the wedge shaped volume to the inspiratory tube (See FIG. 1) at a junction 109. The adapter 130 is referred to as semi-cylindrical because, in the illustrated embodiment, it includes a substantially cylindrical portion 220 and a wedge portion 222 joined at a first seam 223, both of which are open at their respective bottoms to the interior of the variable volume bounded by plates 210 and bellows 214. A top edge 221 of the front plate 210 is joined with the apex of the wedge portion 222. The cylindrical portion 220 and the wedge portion 222 are both connected to the top of the bellows at a common, second seam 224 to thereby close the variable volume.

In an embodiment, the top edge (i.e., the horizontal length) of plate 210 (and, hence, of adapter 130) is in the range of six to fourteen inches, and preferably about ten inches long. The vertical dimension (height) of the plate 210 and the bellows section 214 is also in the range of six to fourteen inches, and preferably about ten inches. In the fully open position, the length of the second seam 224, i.e., the distance between the respective top edges of the front and back plates 210, is in the range of about one to three inches, and preferably about two inches. In the contracted (closed) position, the separation between the top horizontal edges of the opposing plates 210 is in the range of zero to two inches, and preferably about ¾ inches.

The primary motive sub-system 204 includes respective electromagnets 230(a) and 230(b) mounted to and stationary within the ventilator housing 101, and respective magnetic plates 232(a) and 232(b) winch cooperate with the electromagnets 230 to expand and contract the wedge shaped oscillating volume 202 in accordance with user input parameters entered into control panel 118 (FIG. 1). For this purpose, the magnetic plate 232(a) is connected to the oscillating plate 210 by a bracket 234(a); similarly, the magnetic plate 232(b) is connected to the oscillating plate 210 by a bracket 234(b). The electromagnet 230 and plate 232 combination generally functions in a manner analogous to well-known magnetic door locks such as, for example, those available from Door King and described at http://www.doorking.com/access-controls/magnetic-door-locks.php.

In operation, when a current is applied to the electromagnet, 230, a corresponding magnetic field is produced by the electromagnet, which draws the plate 232 toward the electromagnet 230. When the current ceases, the magnetic force quickly decays and terminates the magnetic interaction between the electromagnet 230 and its associated plate 232.

In one embodiment, a first current is applied to the electromagnet 230(a), which draws the plate 232(a) to the left in FIG. 2, thereby reducing the angle 218, closing the bellows 214 and contracting the variable volume within the wedge shaped oscillating volume 202. This contraction causes a positive pressure in the inspiratory tube 108, supplying pressurized gas (e.g., air/oxygen mixture) to the patient's lungs 104 (See FIG. 1). The first current applied to electromagnet 230(a) is reduced or terminated, bringing the inspiratory phase of the oscillating cycle to a close.

A second current is then applied to the electromagnet 230(b), which draws the plate 232(b) to the right in FIG. 2, thereby increasing the angle 218, opening the bellows 214 and expanding the variable volume within the wedge shaped oscillating volume 202. This expansion causes a negative pressure in the expiratory tube 106, removing air from the patients lungs 104 (See FIG. 1). The second current, applied to electromagnet 230(b) is then terminated, bringing the expiratory phase of the oscillating cycle to a close. This process is repeated at high frequency, thereby ventilating the patient, For small patients requiring small air volumes and small pressure amplitudes, the distances traveled by plates 232(a) and 232(b) as wedge shaped oscillating volume 302 expands and contracts may he small enough so that the magnetic fields produced by respective magnets 230(a) and 230(b) are sufficiently strong to draw the plates 232(a) and 232(b) back and forth, without further assistance. That is, during oscillation the plates 232(a) and 232(b) may remain within a sufficiently strong magnetic field produced by magnets 230(a) and 230(b) so that no further motive force is needed to maintain oscillation.

For larger patients requiring larger air volumes and pressure amplitudes, plates 232(a) and 232(b) may travel outside the range of magnetic flux produced by magnets 230(a) and 230(b) needed to maintain oscillation. Consequently, a supplemental motive force may be needed, to "nudge" a plate 234 back into magnetic engagement with its corresponding electromagnet 230.

With, continued reference to FIG. 2, the supplemental motive sub-system 206 may be employed to nudge plate 210 (via plate 232(a)) back into engagement with electromagnet 230(a) during the inspiratory phase corresponding to contraction of the wedge shaped oscillating volume 202. Similarly, the supplemental motive sub-system 206 may be employed to nudge plate 210 (via plate 232(b)) back into engagement with electromagnet 230(b) during tire expiratory phase corresponding to expansion of the wedge shaped oscillating volume 202.

Alternatively, one or both of the primary and supplemental motive sub-systems may comprise only a single magnet (or motor), coupled with a spring, elastic, or gravitational component configured to oppose the single magnet (or motor) to facilitate the expansion and contraction of the variable volume.

Figure 3:
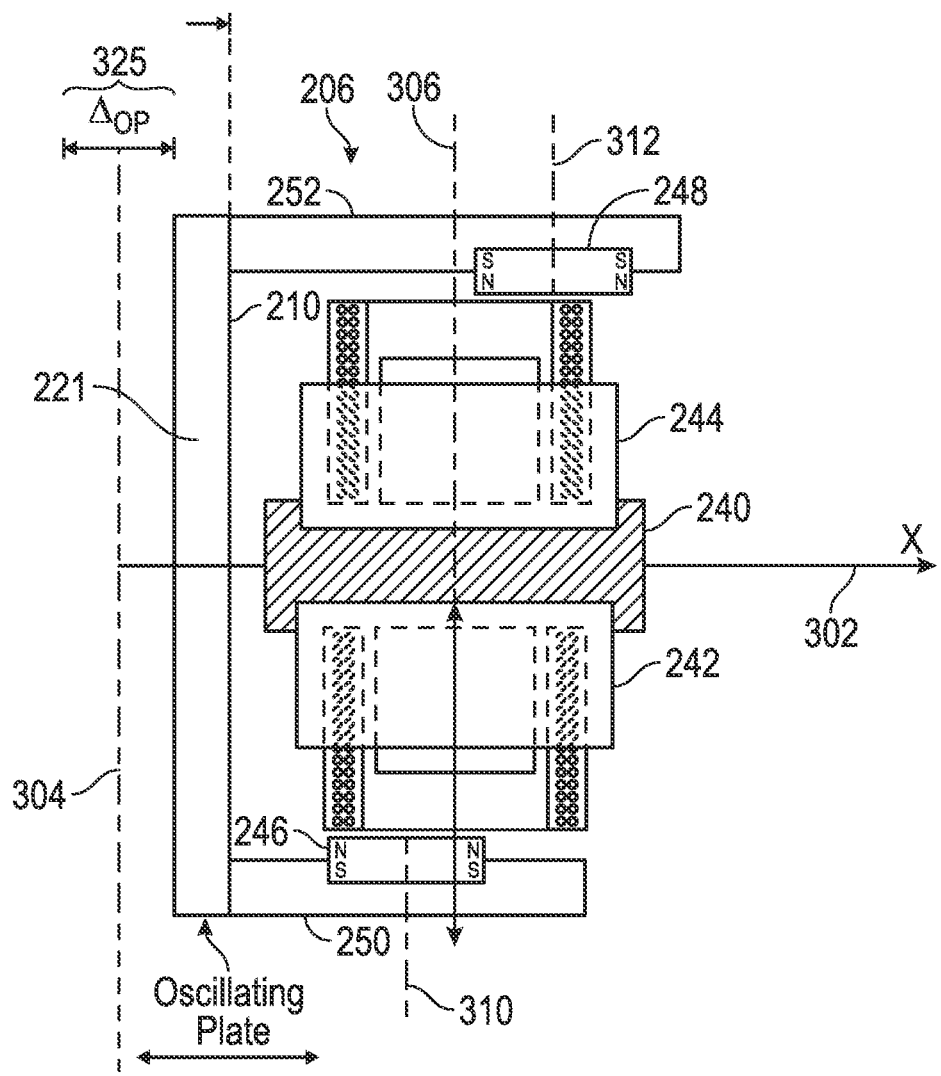
FIG. 3 is a schematic cross-section view of the inspiratory and expiratory nudge assemblies in accordance with an embodiment.

More particularly and also referring now to FIG. 3, the supplemental motive sub-system 206 includes an inspiratory coil 242 mounted on one side of a yoke 240, and an expiratory coil 244 mounted on the other side of the yoke 240. As explained in greater detail below, the inspiratory coil 242 is configured to nudge an inspiratory magnet 246 connected to the plate 210 via a bracket 250; similarly, the expiratory coil 244 is configured to nudge an expiratory magnet 248 connected to the plate 210 via a bracket 252. In a preferred embodiment, respective magnets 246 and 248 are rare earth magnets.

With continued reference to FIGS. 2 and 3, a first reference line 302 extends from left to right through the center of the yoke 240 and defines an X direction. A second reference line 306 extends top to bottom (along a Y direction) through the centerline of respective coils 242 and 244. In the illustrated embodiment, the second reference line 306 is orthogonal to the first reference line 302. A third reference line 304 (also extending in the Y direction) represents the nominal position pa midpoint) of plate 210, i.e., when plate 210 is half way between Its extended position (to the right in FIGS. 2 and 3) and its contracted position (to the left in FIGS. 2 and 3).

In the position shown in FIG. 3, the plate 210 is in the folly expanded position, i.e., the plate 210 is to the right of the centerline 304 in tins position, the expiratory phase has concluded, and the inspiratory phase is about to begin. As briefly discussed above, if the plate 232(a) is sufficiently close to the electromagnet 230(a) to draw the plate 210 to the left and thereby commence the inspiratory phase, it may not be necessary to use supplemental motive sub-system. 206. However, in the event plate 232(a) is outside the effective magnetic range of the electromagnet 230(a), it may be desirable to use the supplemental motive sub-system 206 to nudge the plate 210 to the left, thereby bringing the plate 232(a) into magnetic engagement with electromagnet 230 (a). The range between the far left position of the plate 210 contracted) and the far right position of the plate 210 (expanded) is referred to as the delta $P_W$, delta pressure, or $\Delta P_W$ associated with the oscillation of wedge shaped oscillating volume 202.

Also in the position shown in FIG. 3, a centerline 310 of the magnet 246 is positioned to the left of the reference line 306. By selectively applying current to the inspiratory coil 242, such that the magnetic "north" end of the coil 242 along the reference line 306 opposes the "north" end of magnet 246, the magnet 242 will be urged (magnetically) to the left, initiating the inspiratory (contraction) phase and nudging the plate 232(a) into magnetic engagement with the electromagnet 230(a) to thereby complete the inspiratory phase. In the process, the top edge 221 of the plate 210 (see FIG. 3) moves from right to left, crossing over to the left, side of the reference line 304.

Upon completion of the inspiratory phase the wedge shaped oscillating volume 202 is contracted and the plate 210 is at its left most position. Again, if the plate 232(b) is sufficiently close to the electromagnet 230(b) to draw the plate 210 to the right and thereby commence the expiratory phase, it may not be necessary to use supplemental motive sub-system 206. However, in the event plate 232(b) is outside the effective magnetic range of the electromagnet 230(b), it may be desirable to use the supplemental motive sub-system 206 to nudge the plate 210 back to the right, thereby bringing the plate 232(b) back into magnetic engagement with electromagnet 230(b).

By selectively applying current to the expiratory coil 244, such that the magnetic "north" end of the coil 244 along the reference line 306 opposes the "north" end of magnet 248, the magnet 244 will be urged (magnetically) to the right, initiating the expiratory (expansion) phase and nudging the plate 232(b) back into magnetic engagement with the electro-magnet 230(b) to thereby complete the expiratory phase. In the process, the top edge 221 of the plate 210 moves from left to right, crossing over to the right side of the reference line 304.

In the context of the present disclosure, the term "slew rate" refers to the time delay between the application of current to the electromagnets (or magnetic coils) and the resulting build-up of magnetic flux, as well as the time delay between terminating current to the electromagnets (or magnetic coils) and the collapse of the magnetic flux. Those skilled in the art will appreciate that appropriate pulse width modulation (PWM), proportional integral-derivative (PID), and other control schemes may he employed to account for the slew rates associated with the hardware used to implement the invention.

Figure 4:
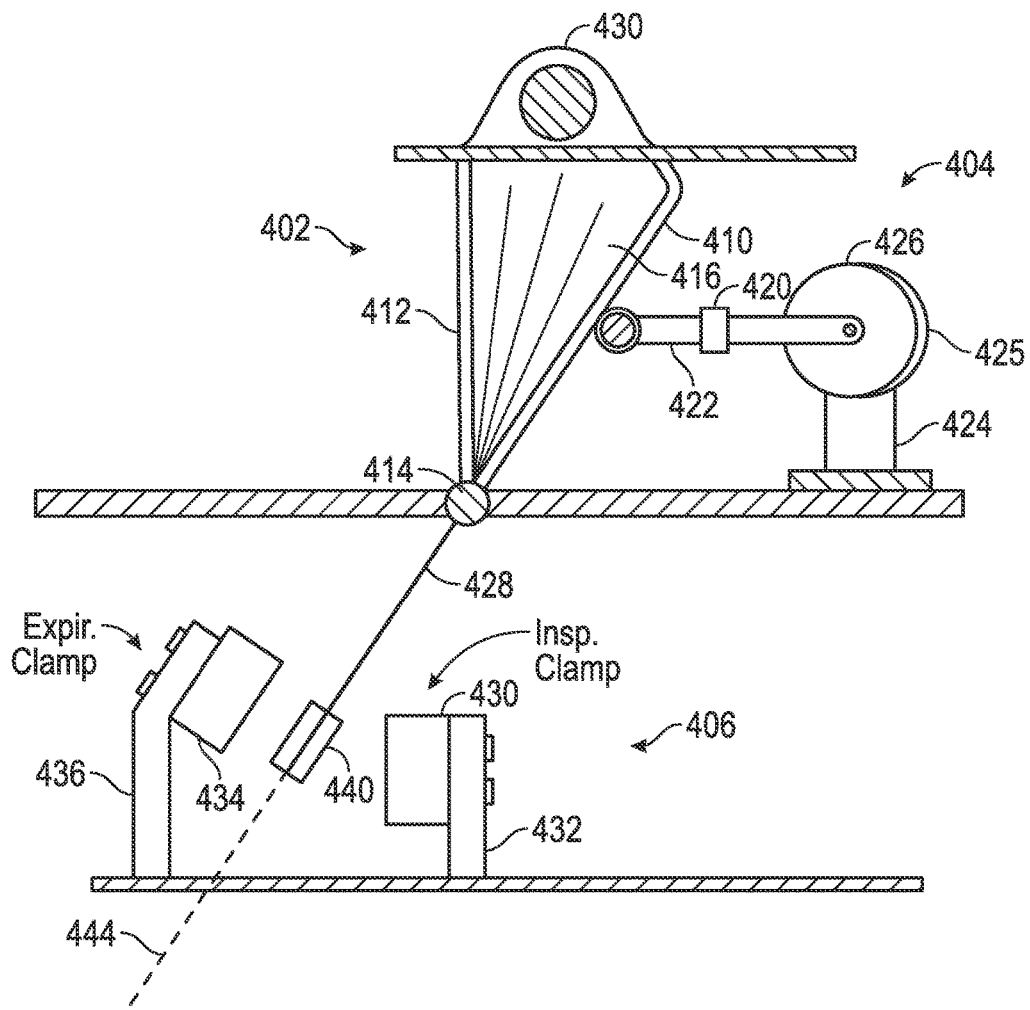
FIG. 4 is a schematic cross-section view of a wedge volume assembly including primary and supplemental motive sub-systems in accordance with an alternate embodiment.
Figure 5:
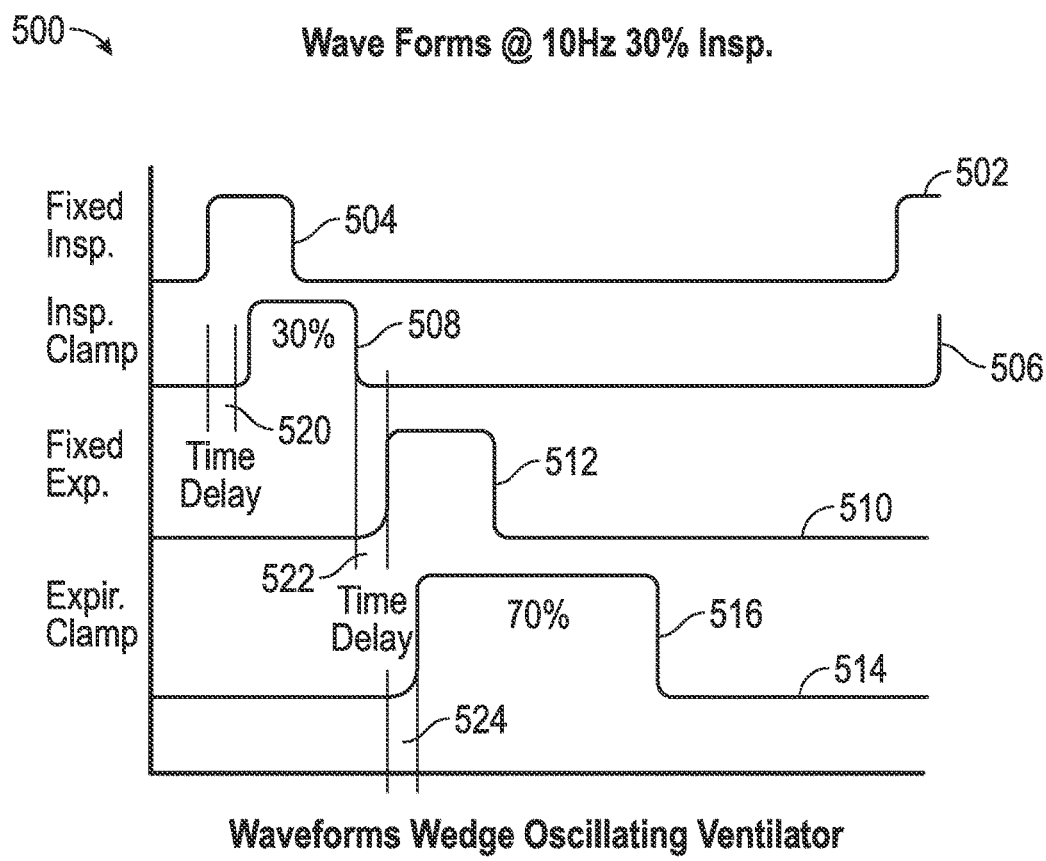
FIG 5 is a graph of exemplary wave forms useful in implementing inspiratory and expiratory phases for pulmonary ventilation in accordance with an embodiment.

An alternate embodiment of the invention is illustrated in FIGS. 4 and 5. More particularly, FIG. 4 is a schematic cross-section view of a variable volume wedge assembly 402, a primary motive sub-system 404, and a supplemental motive sub-system 406 in accordance with an alternate embodiment. The variable volume wedge assembly 402 includes a pivoting plate 410, a stationary plate 412a bellows 416, and an adapter 430.

The primary motive sub-system 406 includes a double-sided plate 440 disposed at the end of a pivoting shaft 428 which may be an extension of the plate 410 configured to pivot about a fulcrum 414. The primary motive sub-system 404 further includes an inspiratory electromagnet 430 secured to the ventilator housing by a mount 432, and an expiratory electromagnet 434 secured to the ventilator housing by a mount 436.

The supplemental motive sub-system 404 includes a fixed inspiratory cod 425 secured to the ventilator housing by a mount 424, and an associated magnet 426 connected to the plate 410 by a shaft 422 and configured to slide from left to right (and vice versa) through a frictionless or near frictionless bearing 420. The fixed expiratory coil and associated magnet are omitted for clarity.

A reference line 444 denotes the mid-range position of the plate 410 and, hence, of shaft 428 approximately halfway between the expanded and contracted position of the variable volume wedge assembly 402. This position corresponds to the midpoint of either the expiratory phase or the inspiratory phase, depending on the direction of travel of the shaft 428. If the plate 440 is sufficiently close to cither electromagnet 430 or 434 to draw the plate magnet 440 in the direction of desired travel, it may not be necessary to use supplemental motive sub-system 406.

However, In the event plate 440 is outside the effective magnetic range of the next electromagnet to be engaged, it may be desirable to use the supplemental motive sub-system 404 to nudge the plate 410 either to the right or to the left, thereby bringing the plate 440 into magnetic engagement with appropriate electromagnet 430 or 434, as described above in connection with FIGS. 2 and. 3.

By selectively applying current to the inspiratory coil 425, for example, such that the magnetic "north" end of the coil 425 opposes the "north" end of magnet 426, the magnet 426 will be urged (magnetically) to the left, completing the inspiratory (contraction) phase and nudging the plate 440 into magnetic engagement with the electromagnet 430.

Upon completion of the inspiratory phase the wedge shaped oscillating volume 402 is contracted and the plate 410 is at its left most position. Again, if the plate 440 is sufficiently close to the electromagnet 434 at this juncture to draw the plate 440 back toward the electromagnet 434 upon application of current to the electromagnet 434, it may not be necessary to use supplemental motive sub-system 404. However, in the event plate 440 is outside the effective magnetic range of the electromagnet 434, it may be desirable to use the supplemental motive sub-system 406 to nudge the plate 440 back into magnetic engagement with electromagnet 434. Those skilled in the art will appreciate that the pressure of the wave increases or decreases as a function of the distance between plate 440 and the magnets 435, 434.

By selectively applying current to the expiratory coil (hidden from view in FIG. 4), the plate 410 is nudged to the right, initiating the expiratory (expansion) phase and nudging the plate 410 back into magnetic engagement with the electromagnet 434 to thereby complete the expiratory phase.

FIG 5 is a graph 500 of exemplary wave forms useful in implementing inspiratory and expiratory phases for pulmonary ventilation in accordance with an embodiment. More particularly, a first waveform 502 including a current application segment 504 may be applied to a first nudge coil of a supplemental motive sub-system to initiate an inspiratory phase. Following a predetermined time delay 520, a second waveform 506 including a current application segment 508 maybe applied to a first electromagnet of a primary motive sub-system to complete the inspiratory phase.

Following a predetermined time delay 522, a third waveform 510 including a current application segment 512 may be applied to a second nudge coil of the supplemental motive sub-system to initiate the expiratory phase. Following a predetermined time delay 524, a fourth waveform 514 including a current application segment 516 may be applied to a second electromagnet of a primary motive sub-system to complete the expiratory phase. In the illustrated embodiment, the inspiratory phase (e.g., the current application segment 508 coupled with time delay 520) is in the range of about a 30% duty cycle, and the expiratory phase (e.g., the current application segment 516 coupled with time delay 524) represents in the range of about 70% of the total duty cycle.

A pulmonary ventilator is provided winch includes a housing having a user interface control panel; a pneumatic circuit for delivering a high frequency pressure wave from the housing to a patient lung; a variable volume disposed within the housing including a stationary plate secured to the housing and a reciprocating plate pivot ably mounted with respect to the stationary plate; and a magnet assembly disposed within the housing and configured to pivot the reciprocating plate. The variable volume may also include a resiliently contractible section extending between and joining a portion of the stationary plate and a portion of the reciprocating plate, wherein the resiliently contractible section may be in the form of a bellows and/or a pleated material.

In an embodiment, one or both of the stationary plate and the reciprocating plate may comprise a triangular, rectangular; or trapezoidal shape, and the variable volume may be wedge shaped.

The pulmonary ventilator may include an adapter configured to enclose the stationary plate and the reciprocating plate, and to communicate the pressure wave from the variable volume to the pneumatic circuit. The adapter may be semi-cylindrical.

In an embodiment, the magnet assembly includes a primary motive sub-system for repeatedly pivoting the reciprocating plate back and forth, to thereby increase and decrease the variable volume. The primary motive sub-system may comprise a first electromagnet and a first plate configured for magnetic interaction with the first electromagnet. The primary motive sub-system may further comprise a second electromagnet and a second plate configure for magnetic interaction with the second electromagnet, where the first electromagnet is configured to cause expansion of the variable volume and the second electromagnet is configured to cause contraction of the variable volume.

The pulmonary ventilator may also include a supplemental motive sub-system configured to nudge the reciprocating plate into magnetic engagement with the primary motive sub-system, wherein the supplemental motive sub-system may comprise a first permanent magnet and a first coil configured for magnetic interaction with the first permanent magnet, and the first permanent magnet may be a rare earth magnet.

In another embodiment, the primary motive sub-system comprises an inspiratory electromagnet and an expiratory electromagnet, and the supplemental motive sub-system comprises an inspiratory coil and an expiratory coil.

A pulmonary ventilator is also provided which includes a variable volume disposed within a housing, the variable volume having a movable surface; a pneumatic circuit for delivering a high frequency pressure wave from the variable volume to a patient; a primary motive sub-system for oscillating the movable surface; and a supplemental motive sub-system configured to nudge the movable surface into engagement with the primary motive sub-system.

In an embodiment, the primary motive sub-system may include at least one electromagnet, and the supplemental motive sub-system may include at least one magnetic coil.

In another embodiment, the movable surface comprises a reciprocating plate and a bellows extending between and joining a portion of a stationary plate and a portion of a reciprocating plate; the primary motive sub-system and the supplemental motive sub-system are connected to the reciprocating plate; the primary motive sub-system, comprises an inspiratory electromagnet, and an expiratory electromagnet, and the supplemental motive sub-system comprises an inspiratory coil arid an expiratory coil.

A method of oscillating a variable volume having a movable plate to generate a high frequency pressure wave for use in pulmonary ventilation is also provided. The method includes actuating a supplemental motive sub-system to midge the movable plate into magnetic engagement with a primary motive sub-system, and actuating the primary motive sub-system to alternately expand and contract the variable volume.

In one embodiment of the method, the variable volume comprises a resiliently contractible section extending between and joining a portion of a stationary plate and a portion of the movable plate which is pivotably mounted with respect to the stationary plate, and the supplemental motive sub-system comprises an electromagnet and the supplemental motive sub-system comprises a magnetic coil. In the method, the step of actuating the supplemental motive sub-system may involve applying a first waveform to the magnetic coil; and the step of actuating the primary motive sub-system may involve applying, after a predetermined period of delay following application of the first waveform to the magnetic coil, a second waveform to the electromagnet The foregoing description is merely illustrative in nature and is not intended to limit the embodiments of the subject matter or the application and uses of such embodiments. Furthermore, there is no intention to be bound by any expressed or implied theory presented in the technical field, background, or the detailed description. As used herein, the word "exemplary" means "serving as an example, instance, or illustration." Any implementation described herein as exemplary is not necessarily to be construed as preferred or advantageous over other implementations, and the exemplary embodiments described herein are not intended to limit the scope or applicability of the subject matter in any way.

Embodiments of the subject matter may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. In this regard, it should be appreciated that the various block components shown m the figures may be realized by any number of hardware, software, and/or firmware components configured to perform the specified functions.

For example, an embodiment of a system or a component may employ various integrated circuit components, e.g., memory elements, digital signal processing elements, logic elements, look-up tables, or the like, which may carry out a variety of functions under the control of one or more microprocessors or other control devices. In this regard, the subject, matter described herein can be implemented in the contest of any computer-implemented system and/or in connection with two or more separate and distinct computer-implemented systems that cooperate and communicate with one another.

While at least one exemplary embodiment, has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A pulmonary ventilator, comprising:
   a housing including a user interface control panel;
   a pneumatic circuit for delivering a high frequency pressure wave from the housing to a patient lung;
   a wedge shaped variable volume disposed within the housing and including a stationary surface secured to the housing and a pivoting surface pivotably mounted with respect to the stationary surface; and
   a primary motive sub-system including a magnet assembly disposed within the housing, the magnet assembly including an electromagnet configured to drive a magnetic plate to thereby rotate the pivoting surface through a variable arc about a pivot line;
   wherein the high frequency pressure wave exhibits a frequency greater than a patient breathing cycle.

2. The pulmonary ventilator of claim 1, wherein the stationary surface and the pivoting surface each comprise one of a triangular, rectangular, and trapezoidal shape.

3. The pulmonary ventilator of claim 1, wherein the variable volume further comprises a resiliently contractible section extending between and joining a portion of the stationary surface and a portion of the pivoting surface.

4. The pulmonary ventilator of claim 3, wherein the resiliently contractible section comprises a bellows.

5. The pulmonary ventilator of claim 3, wherein the resiliently contractible section comprises a pleated material.

6. The pulmonary ventilator of claim 1, further comprising an adapter configured to enclose the stationary surface and the pivoting surface and to communicate the pressure wave from the variable volume to the pneumatic circuit.

7. The pulmonary ventilator of claim 6, wherein the adapter is semi-cylindrical.

8. A pulmonary ventilator, comprising:
   a housing including a user interface control panel;
   a pneumatic circuit for delivering a high frequency pressure wave from the housing to a patient lung;
   a wedge shaped variable volume disposed within the housing including a stationary plate secured to the housing and a reciprocating plate pivotably mounted with respect to the stationary plate; and
   a magnet assembly disposed within the housing and configured to rotate the reciprocating plate through a variable arc about a pivot line;
   wherein the magnet assembly comprises a primary motive sub-system for repeatedly pivoting the reciprocating plate back and forth to thereby increase and decrease the variable volume.

9. The pulmonary ventilator of claim 8, wherein the primary motive sub-system comprises a first electromagnet and a first plate configured for magnetic interaction with the first electromagnet.

10. The pulmonary ventilator of claim 9, wherein the primary motive sub-system further comprises a second electromagnet, and a second plate configured for magnetic interaction with the second electromagnet, and further wherein the first electromagnet is configured to cause expansion of the variable volume and the second electromagnet is configured to cause contraction of the variable volume.

11. The pulmonary ventilator of claim 8, further comprising a supplemental motive sub-system configured to nudge the reciprocating plate into magnetic engagement with the primary motive sub-system.

12. The pulmonary ventilator of claim 11, wherein the supplemental motive sub-system comprises a first permanent magnet and a first coil configured for magnetic interaction with the first permanent magnet.

13. The pulmonary ventilator of claim 12, wherein the first permanent magnet is a rare earth magnet.

14. The pulmonary ventilator of claim 11, wherein the primary motive sub-system comprises an inspiratory electromagnet and an expiratory electromagnet, and wherein the supplemental motive sub-system comprises an inspiratory coil and an expiratory coil.

* * * * *